United States Patent [19]

Mitrani

[11] Patent Number: 5,380,310
[45] Date of Patent: Jan. 10, 1995

[54] DISPOSABLE SANITARY ARTICLE FOR INCONTINENT PERSONS

[75] Inventor: Sem Mitrani, Ris Orangis, France

[73] Assignee: Kaysersberg, S.A., France

[21] Appl. No.: 670,385

[22] Filed: Mar. 15, 1991

Related U.S. Application Data

[63] Continuation of Ser. No. 854,546, Apr. 21, 1986, abandoned, which is a continuation of Ser. No. 577,630, Jan. 31, 1984, abandoned.

[30] Foreign Application Priority Data

Jun. 2, 1982 [FR] France ................... 82-09591

[51] Int. Cl.⁶ ............ A61F 13/15; A61F 13/20; A61F 5/44
[52] U.S. Cl. ................ 604/385.1; 604/358; 604/347; 604/349
[58] Field of Search .............. 604/385.1, 346–349, 604/358

[56] References Cited

U.S. PATENT DOCUMENTS

| | | | |
|---|---|---|---|
| 3,731,688 | 5/1973 | Litt et al. | 604/385.1 X |
| 3,868,287 | 2/1975 | Lewyckyj | 156/201 |
| 3,874,385 | 4/1975 | Gellert | 604/385.1 X |
| 3,927,674 | 12/1975 | Schaar | 604/385.1 |
| 3,958,574 | 5/1976 | Rohr | 604/385.1 X |
| 3,968,798 | 7/1976 | Hokanson | 128/284 |
| 3,978,861 | 9/1976 | Schaar | 604/385.1 |
| 4,108,179 | 8/1978 | Schaar | 604/385.1 |
| 4,453,938 | 6/1984 | Brendling | 604/346 |
| 4,475,912 | 10/1984 | Coates | 604/385.1 |
| 4,560,380 | 12/1985 | Tharel | 604/385.1 |
| 4,573,990 | 3/1986 | Ohsaki | 604/385.1 |

FOREIGN PATENT DOCUMENTS

| | | | |
|---|---|---|---|
| 2289131 | 5/1976 | France . | |
| 2433936 | 3/1980 | France . | |
| 2443739 | 3/1975 | Germany | 604/385 |
| 1543915 | 4/1979 | United Kingdom | 604/385 |

Primary Examiner—Randall L. Green
Assistant Examiner—Elizabeth M. Burke
Attorney, Agent, or Firm—Breiner & Breiner

[57] ABSTRACT

A disposable sanitary article for incontinent persons, with a substantially rectangular configuration.

This article includes an absorbing pad 3, an impermeable external sheet 2, and a permeable inside sheet 4. The longitudinal edges (b, b') are folded back on the permeable inside surface. This configuration is kept in place at each end by a permanent fastening means, in particular a bead of adhesive 7, and provides a pouch effect in use.

Use of this article for incontinent adult males with fastening to any kind of underwear.

8 Claims, 3 Drawing Sheets

DISPOSABLE SANITARY ARTICLE FOR INCONTINENT PERSONS

This is a continuation of co-pending application Ser. No. 06/854,546 now abandoned on Apr. 21, 1986, which is a continuation of application Ser. No. 06/577,630 filed Jan. 31, 1984, now abandoned.

The present invention concerns a disposable, absorbing article for incontinent persons, and more particularly adult males.

Many solutions have been suggested to solve the problem of the incontinent adult, and in particular male incontinence.

One of the palliatives consists in providing a urine-receiving pouch which can be fitted to the incontinent man. Various types have been described, in particular in French Patent No. 2,312,228. This patent relates to a pouch fitted to briefs, especially designed for this purpose, using button-type closing means.

This pouch acts as a housing for the male organs and as a container for the liquids. It includes an impermeable plastic external sheath and possibly, too, an absorbing inside cladding. However, special underwear is required because the pouch only fits this special clothing.

Other products for incontinent persons are absorbing sanitary articles. In fact, these are diapers or pilches fitted to adult size. Such articles are described in a number of patents, in particular in U.S. Pat. No. 4,018,226; French Patent No. 2,419,039, French Patent No. 2,443,831, or are on the market.

One of these products is rectangular in shape and assumes an inverted-pleat configuration, the pleats being kept in place by two adhesive spots in the central part of this article, in the crotch area. The pleats open up in the area of the wearer's waist, fastening being implemented by an adhesive tape in that area.

The described articles, clothes, and diapers of the prior art as well as those on the market incur one or more drawbacks. The pouches are fairly bulky and unpleasant to wear. They are more suited in a hospital than for ambulatory uses.

The changes or sanitary sets are large, about the size of adult slacks, and accordingly unpleasant to wear for the ambulatory. Furthermore, just like the "pouches," they cause some esthetic embarrassment to the wearer because of their being thick.

The replacement of a soiled sanitary set requires various handling within the hospital on the part of the nurse who must lift the sick to change him.

Such a sanitary set is no easier in ambulatory use, being fastened to the waist. Various operations are required for the wearer to remove a used set, namely to remove at least partly the clothes or underwear covering this sanitary set.

Furthermore, wearing a wet product applied to a large area is unpleasant even for a short time. Lastly, the possibility of leaks, aside from material damages, unsettles the incontinent person.

The sanitary article of the invention allows overcoming these drawbacks by providing the advantages of the pouch and pilch for adults without incurring said defects.

In particular the sanitary article of the invention is comfortable due to its smaller dimensions and its good adaptation to the male anatomy. It is easy to use both in the hospital and in ambulatory manner, being easy to apply and to remove in particular in view of its small size and the ease of fixation. Furthermore, it provides high hermeticity because of its absorbing power related to its pouch effect when put in place, providing the incontinent person with a sense of security. Also, it adapts to a wide range of underwear and clothes, even to sports clothes, and advantageously no special garment is called for by the sanitary article of the invention.

The object of the present invention is a disposable sanitary article meant to absorb body liquids, in particular for incontinent adult males, of the type including an absorbing pad, a liquid-impermeable external sheet, a liquid-permeable inside sheet, the overall shape being substantially rectangular, with the longitudinal edges being folded back on the permeable inside surface, forming longitudinal folds, this configuration being kept in place at each end by a permanent fastening means, and with a pouch effect that is well suited to the male anatomy.

The impermeable external sheet and the permeable inside sheet advantageously are fastened to each other at their lateral parts along longitudinal selvages in such a manner that the outside hem consists of an impermeable external sheet defining a central zone covered by the permeable inside sheet.

The two longitudinal hems folded back toward each other can be arranged to be substantially mutually adjacent and to be on either side of the longitudinal axis of symmetry of the diaper. In a variation, there may be a gap between the hems to provide a longitudinal pouch opening where the article is flat before use. In another embodiment of the invention, the longitudinal edges of the hems overlap at least partly.

The fastening means include, for instance, adhesive tapes, narrow strips of adhesive, hot thermofusion, or any other means. The fastening means also can consist of a flap transverse to each article end. The flap consists of the impermeable external sheet adhering to the permeable inside sheet while being of the same configuration as the overall article, namely the longitudinal edges being folded over the permeable inside surface. The absorbing pad does not extend into the flap, but constitutes its adjacent surface. However, this solution is not advantageous in the manufacturing plan.

The sanitary article of the invention also includes at least one adhesive element fixed to the outside of the impermeable sheet covering the outer surface of the absorbing pad and preferably located in the front zone of the sanitary article, in particular on its center line.

Such an adhesive element may be an adhesive tape protected before use by a siliconized paper.

The length of this tape may be up to half that of the sanitary article, and extends for instance from its center to the pleat of the flap.

When the sanitary article is being used, this adhesive tape allows easily fixing the front part of the sanitary article to the underwear, or even the outer garb of the wearer.

A pouch effect is obtained from the configuration of the longitudinal folds kept in place at the ends together with the sanitary article being fastened to the underwear by its lower end. When put into place, the longitudinal folds of the sanitary article are tensioned and spread apart. The lower surface of the sanitary article forms an inward curve, the entire set forming a pouch perfectly adapting to the male anatomy.

Furthermore, the combination of an impermeable external sheet with the outer edges of the equally impermeable longitudinal folds ensures high hermeticity to such an article.

Again, the absorbing inside elements of the article retain the urine and, in case of saturation, the pouch effect prevents the liquids from leaking.

In one embodiment of the invention, the longitudinal folds are of the single kind, that is they are obtained by merely folding over the lateral parts of the sanitary article along a folding line parallel to the longitudinal direction of the article.

In the preferred embodiment of the invention, the sanitary article comprises "double" longitudinal folds, with an S-shaped cross-section, which are obtained by doubly folding back each lateral part of the sanitary article, thereby imparting to the overall set an inverted-pleat configuration. In this case the panels adjacent to the central strip are fastened at their lateral ends to the lateral ends of said central strip. The external panels can be free or fixed to the adjacent panels in similar manner.

One article of the invention is manufactured by a method known per se in the field of absorbing articles.

Bonding the permeable and impermeable sheets at their longitudinal ends may be delayed during the first stage, taking place only after forming the inverted or single fold configuration by heat-sealing. The external impermeable sheet is fastened to the permeable inside sheet in the lateral parts of the sanitary article, along longitudinal selvages, by gluing or by heat-sealing.

The invention will be more clearly understood and its advantages will become clearer in relation to the description below of two non-restrictive illustrative embodiments of the object of the invention and the attached drawings.

Figure 1:
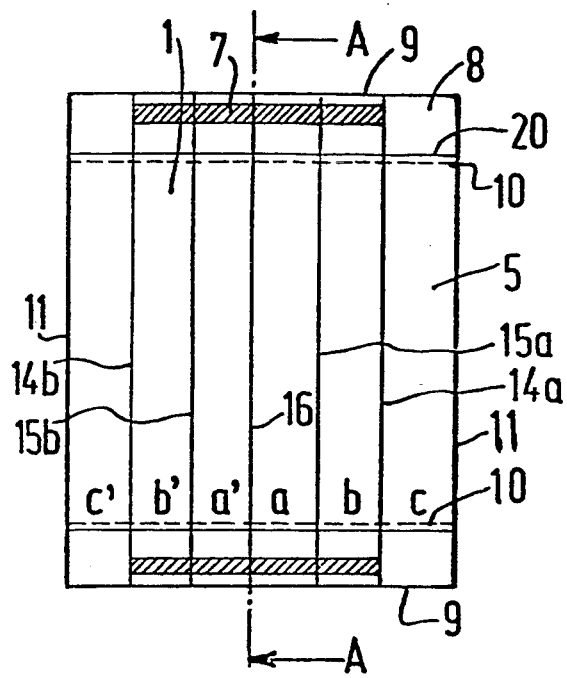
FIG. 1 is a top view of an article of the invention prior to folding.

The reference numerals denote analogous elements the various figures.

Reference 1 denotes the overall sanitary article of the invention.

Figure 2:
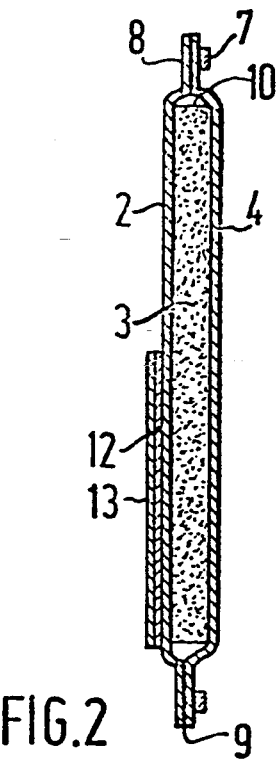
FIG. 2 is a longitudinal section along AA of the article of FIG. 1.

Article 1 shown in FIGS. 1 and 2 is an absorbing article of rectangular configuration comprising an external rectangular sheet 2, also called the support sheet, which consists of a liquid-impermeable plastic, an absorbing pad 3 which is also rectangular but slightly shorter than the external sheet on which it is centered, and a liquid-permeable inside sheet 4 covering the absorbing pad.

The sheet 4 is also centered on the external sheet 2 and preferably is of the same length.

The absorbing pad 3 illustratively can be a pad of cellulose foam, widely called "fluff."

The impermeable sheet 2 is made of a plastic such as polyethylene, polypropylene, polychloride vinyl, etc.

The permeable sheet 4, for instance, is a non-woven material.

In the drawing of FIG. 1, the absorbing pad is bounded at each end by a line 10. The inside sheet 4 and the impermeable sheet 2 come together and are welded to each other beyond the edges 10 in order to form the extensions 8 themselves bounded by the lateral ends 9 of article 1. A folding line 20 may be provided transversely near these extensions in case they are desired to be folded back.

An adhesive tape 12 covered with a siliconized protective paper 13 is deposited on the external sheet 2. Thin lines 14a, 14b, 15a, 15b and 16 define panels of essentially equal areas a, b, c and a', b', c', the line 16 along the axis AA dividing the surface at its center.

A bead of adhesive 7 is applied transversely in the zone of the extensions 8 and at least in the zone of panels a, a', b, b'.

Figure 3:
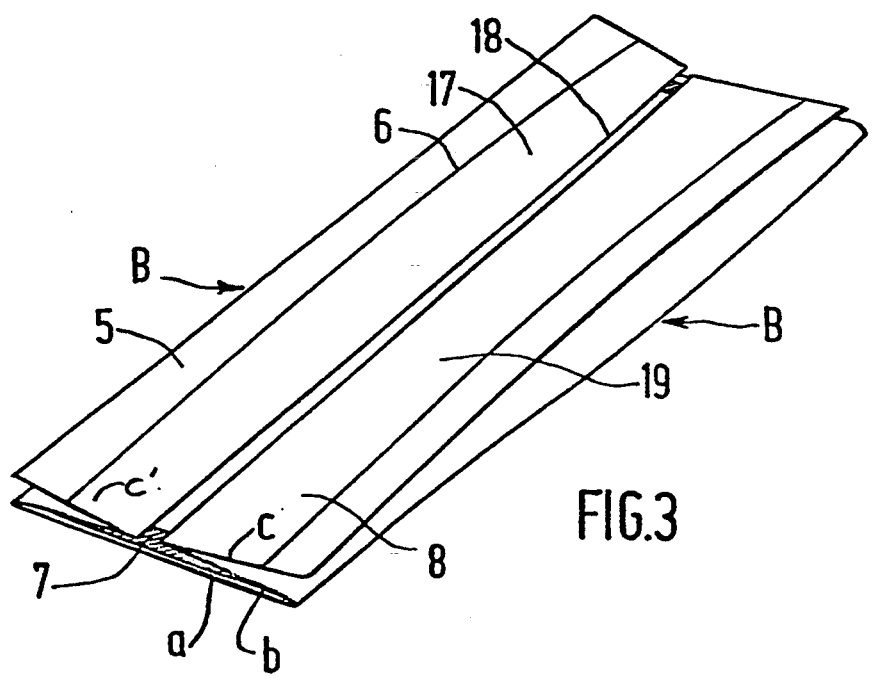
FIG. 3 is a perspective of an article of the invention after folding.

FIG. 3 is an overall view of article 1 when assembled by folding the initially flat article described in FIG. 1.

FIG. 3 shows the panels c and c' which constitute the upper sides 19 of the lateral folds which were pleated along 14a, 14b and 15a, 15b, the panels c and c' covering the panels b and b' which in turn cover the panels a and a', with the upper sides of the folds c and c' meeting edge against edge.

Figure 4:
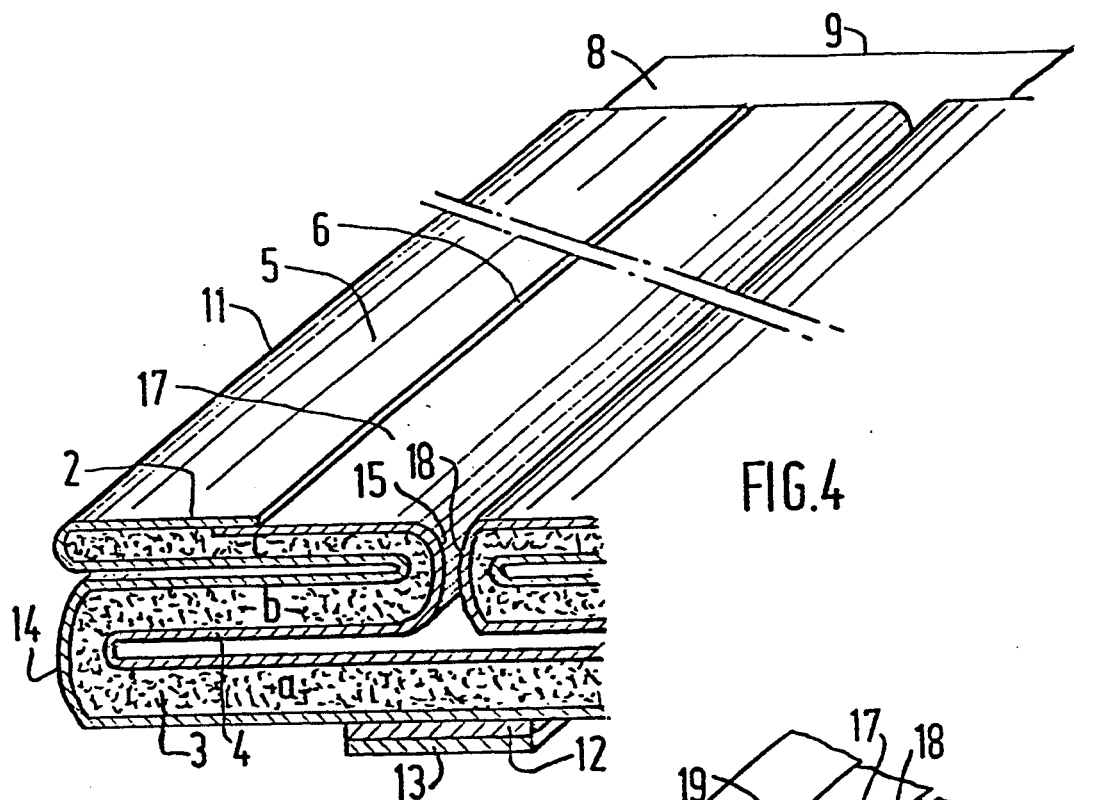
FIG. 4 is a cross-section along BB of the article of FIG. 3.

FIG. 4 is a cross-section of FIG. 3 along BB, showing the above-described elements, in particular the panels a, b, c in their position of S-shaped double fold.

The line 6 represents the edge of the lateral part 5 of the impermeable external sheet 2 which encloses the outer edge of the pad and is returned to the upper side of this pad covered by the permeable inside sheet. The lateral part 5 is bonded to the permeable inside sheet along the longitudinal rim 6. The central part 17 of the upper side of the panel c is covered by the permeable inside sheet 4.

The adhesive tape 12 with its siliconized paper 13 is fixed to the impermeable external sheet in the central part of that surface of the sanitary article which faces away from the body of the wearer.

Figure 5:
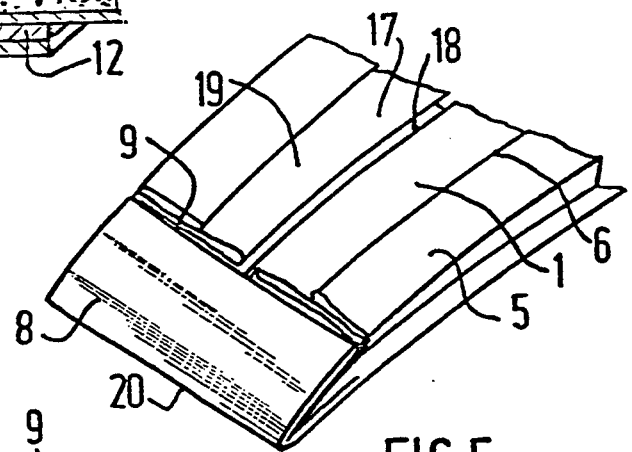
FIG. 5 is a detailed view of an article of the invention following its folding and the folding-back of the ends.

FIG. 5 is a detailed view of the article 1 when the extension 8 is folded back along the fold line 20.

Figure 6:
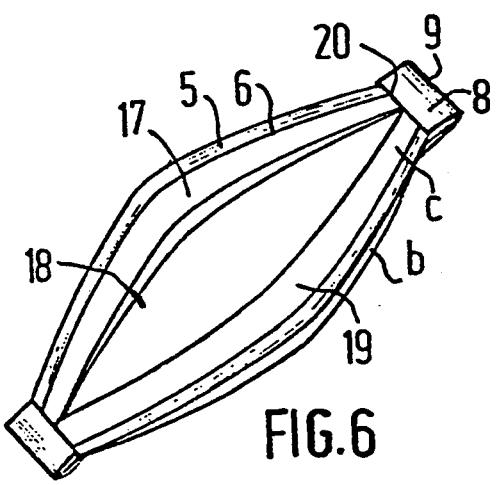
FIG. 6 is a perspective of an article of FIG. 5 being readied for use.

FIG. 6 is perspective view of an article of the invention being readied for use. As the lateral parts 19 are spread apart, an opening 18 is left in the article of which the spread panels a and b form a pouch.

Figure 7:
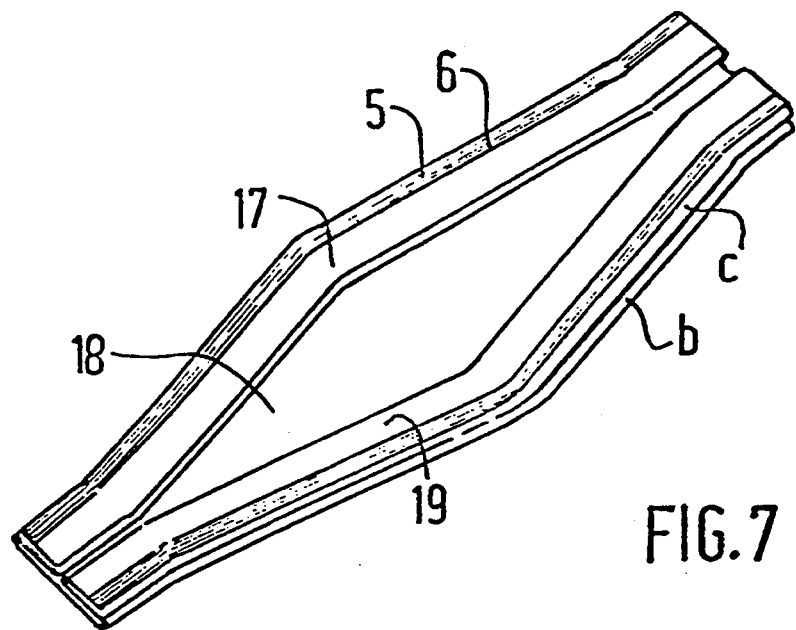
FIG. 7 is a perspective of an article according to FIG. 3, readied for use.

FIG. 7 is a perspective view of another article of the invention described in FIG. 3, the lateral parts 19 being spread apart to form an opening 18.

Figure 8:
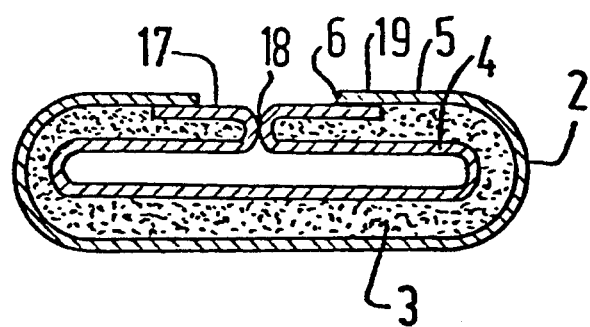
FIG. 8 is a cross-section of a variation of the invention.

In a variation of the invention, the longitudinal folds are of the single type, that is with one side, without folding back on themselves. FIG. 8 is a section of the article in this variation. The panel b covers the panel a. There is no panel c. The permeable sheet 4 is folded beyond the edge of the absorbing pad 3 and constitutes the permeable central part 17 which is fixed to the impermeable external sheet 2 along the selvage 6 of the lateral part 19.

Figure 9:
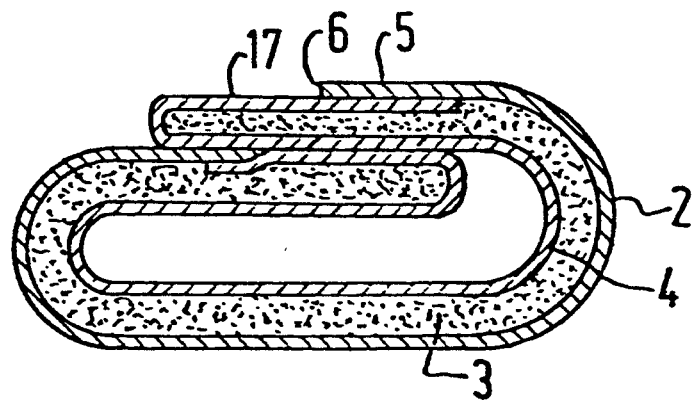
FIG. 9 is a cross-section of another variation of the invention.

In another variation of the invention, the longitudinal folds, whether they be single or double, overlap at least in part. FIG. 9 shows the cross-section of an article of this variation with single folds. They are superposed in the central part; however, this design may incur the inconvenience, due to a fairly thick pad, of being excessively thick. This will not be the case if the folds are of the single type and the configuration of this variation does offer the advantage of higher hermeticity.

Preferable those zones of the sanitary article which are adjacent to the pouch opening 18 remain permeable, while the external parts 5 are impermeable. Therefore, in this sanitary article, the impermeable external sheet is extended beyond the edge 11, or stops within that edge, depending on the longitudinal fold consisting of a cross-sectional S double pleat or of a single pleat.

In the case of a single pleat, whether or not the two rims be superposed, it is the permeable sheet that is folded back beyond the edge, as shown cross-sectionally in FIG. 8.

In the case of a cross-sectional S double pleat, it is the impermeable sheet which is folded back beyond the lateral edge of the sanitary article, as shown cross-sectionally in FIG. 4.

An article of the invention or of one of its variations offers the advantage of reduced size.

Illustratively, but without thereby implying restriction, an article of the invention is 27 cm long, 9 cm wide, and its pad is 1 cm thick. The longitudinal folds, whether single or double, are 4.5 cm wide in such article, with the external impermeable rim being 2.5 cm wide.

I claim:

1. A disposable sanitary article to be worn by incontinent adult males comprising an absorbing pad having a liquid-impermeable sheet attached to an exterior side of said pad and a liquid-permeable sheet attached to an interior side of said pad, said article having an overall substantially rectangular shape with each longitudinal edge of the article being folded back on the liquid-permeable sheet to form longitudinal folds, with each longitudinal edge being secured to a central part of the article at each end of both of said longitudinal folds so as to form a semi-enclosed area, so dimensioned that a portion of said longitudinal folds which is present between each end of each of said longitudinal folds are movable from a position close to the central part to a position spread apart so as to form a pouch so that said liquid-permeable sheet is present within said pouch so that said liquid-permeable sheet comes in contact with a wearer's skin, and wherein said sanitary article is of a size and dimension to encompass external male genitalia but not extend around a wearer's waist so as to absorb fluid emitted from said external male genitalia but not sized to enable said article to collect fecal matter of said adult male and further wherein said sanitary article does not include means for attaching said article around the wearer's waist.

2. Sanitary article of claim 1 wherein each longitudinal edge is secured by a bead of adhesive, or by heat-sealing, or by an adhesive tape.

3. Sanitary article of claim 1 wherein the longitudinal folds are each a single fold and the liquid-impermeable sheet stops at a lateral edge of said single fold.

4. Sanitary article of claim 1 wherein the longitudinal folds are double folds with a cross-sectional S shape and the liquid-impermeable sheet extends beyond each fold of said double fold.

5. Sanitary article of claim 1 wherein each of said longitudinal edges of the longitudinal folds are adjacent.

6. Sanitary article of claim 1 wherein each of said longitudinal edges of the longitudinal folds overlap at least partly.

7. Sanitary article of claim 1 wherein each of said longitudinal edges of the longitudinal folds are spaced apart with a gap therebetween.

8. Sanitary article of claim 1 including at least one adhesive element on the impermeable external sheet.

* * * * *